(12) United States Patent
Frenkel et al.

(10) Patent No.: US 7,547,806 B2
(45) Date of Patent: Jun. 16, 2009

(54) TANNATE SALT OF RASAGILINE

(75) Inventors: Anton Frenkel, Netanya (IL); Tamas Koltai, Netanya (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 0 days.

(21) Appl. No.: 12/002,076

(22) Filed: Dec. 13, 2007

(65) Prior Publication Data

US 2008/0146676 A1   Jun. 19, 2008

Related U.S. Application Data

(60) Provisional application No. 60/875,038, filed on Dec. 14, 2006.

(51) Int. Cl.
*C07C 211/00* (2006.01)
*A61K 31/135* (2006.01)

(52) U.S. Cl. ..................... 564/429; 514/657

(58) Field of Classification Search ............ 564/429; 514/657
See application file for complete search history.

(56) References Cited

U.S. PATENT DOCUMENTS

| | | | |
|---|---|---|---|
| 5,387,612 A | 2/1995 | Youdim et al. | |
| 5,453,446 A | 9/1995 | Youdim et al. | |
| 5,457,133 A | 10/1995 | Youdim et al. | |
| 5,486,541 A | 1/1996 | Sterling et al. | |
| 5,519,061 A | 5/1996 | Youdim et al. | |
| 5,532,415 A | 7/1996 | Youdim et al. | |
| 5,576,353 A | 11/1996 | Youdim et al. | |
| 5,599,991 A | 2/1997 | Youdim et al. | |
| 5,663,415 A | 9/1997 | Chopdekar et al. | |
| 5,668,181 A | 9/1997 | Youdim et al. | |
| 5,744,500 A | 4/1998 | Youdim et al. | |
| 5,786,390 A | 7/1998 | Youdim et al. | |
| 5,891,923 A | 4/1999 | Youdim et al. | |
| 6,126,968 A | 10/2000 | Peskin et al. | |
| 6,277,886 B1 | 8/2001 | Levy et al. | |
| 6,316,504 B1 | 11/2001 | Youdim et al. | |
| 6,462,222 B1 | 10/2002 | Chorev et al. | |
| 6,630,514 B2 | 10/2003 | Youdim et al. | |
| 6,956,060 B2 | 10/2005 | Youdim et al. | |
| 7,309,497 B2 | 12/2007 | Rimpler et al. | |
| 2003/0180332 A1 | 9/2003 | Rimpler et al. | |
| 2004/0127577 A1 | 7/2004 | Blaugrund et al. | |
| 2004/0157784 A1 | 8/2004 | Chopdekar et al. | |
| 2006/0018957 A1 | 1/2006 | Lerner et al. | |
| 2006/0094783 A1 | 5/2006 | Youdim | |
| 2006/0188581 A1 | 8/2006 | Peskin | |
| 2006/0276503 A1 | 12/2006 | Breen et al. | |
| 2007/0100001 A1 | 5/2007 | Youdim et al. | |
| 2007/0112217 A1 | 5/2007 | Frenkel et al. | |
| 2007/0232700 A1 | 10/2007 | Blaugrund et al. | |

FOREIGN PATENT DOCUMENTS

| | | |
|---|---|---|
| WO | 2006057912 | 6/2006 |
| WO | 2007098264 | 8/2007 |
| WO | 2008019871 | 2/2008 |
| WO | 2008076315 | 6/2008 |
| WO | 2008131961 | 6/2008 |

OTHER PUBLICATIONS

U.S. Appl. No. 11/791,684, filed May 24, 2007, Patashnik et al.
U.S. Appl. No. 12/002,082, filed Dec. 13, 2007, Anton Frenkel and Tamas Koltai.
PCT International Search Report issued in PCT International Application No. PCT/US2007/25516, filed Dec. 13, 2007.
U.S. Appl. No. 12/223,794, filed Aug. 7, 2008, Poewe et al.
U.S. Appl. No. 12/283,946, filed Sep. 16, 2008, Lendvai et al.
U.S. Appl. No. 12/231,601, filed Sep. 3, 2008, Oron et al.

*Primary Examiner*—Sikari A Witherspoon
(74) *Attorney, Agent, or Firm*—John P. White; Cooper & Dunham LLP

(57) ABSTRACT

The subject invention provides rasagiline tannate, compositions and a process for manufacture thereof.

13 Claims, 1 Drawing Sheet

TANNATE SALT OF RASAGILINE

The application claims benefit of U.S. Provisional Application No. 60/875,038, filed Dec. 14, 2006, the contents of which are hereby incorporated by reference.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

U.S. Pat. Nos. 5,532,415, 5,387,612, 5,453,446, 5,457,133, 5,599,991, 5,744,500, 5,891,923, 5,668,181, 5,576,353, 5,519,061, 5,786,390, 6,316,504, 6,630,514 disclose R(+)-N-propargyl-l-aminoindan ("R-PAI"), also known as rasagiline. Rasagiline has been reported to be a selective inhibitor of the B-form of the enzyme monoamine oxidase ("MAO-B") and is useful in treating Parkinson's disease and various other conditions by inhibition of MAO-B in the brain. U.S. Pat. No. 6,126,968 and PCT Publication WO 95/11016 disclose pharmaceutical compositions comprising rasagiline salts.

Rasagiline mesylate is approved for treating Parkinson's disease either as monotherapy or as an adjunct with other treatments. See, e.g. AGILECT®, Physician's Desk Reference (2006), 60$^{th}$ Edition, Thomson Healthcare.

The tannate salt of rasagiline or method of its preparation has not been disclosed in the art.

SUMMARY OF THE INVENTION

The subject invention provides rasagiline tannate.

The subject invention also provides a process for manufacture of rasagiline tannate which comprises: a) combining a solution of tannic acid with rasagiline base to form a first mixture; b) removing at least part of the liquid from the first mixture; c) adding a polar, water soluble solvent to the mixture to form a second mixture; and d) completely removing liquid at ambient temperature from the second mixture.

DETAILED DESCRIPTION OF THE INVENTION

Figure 1:
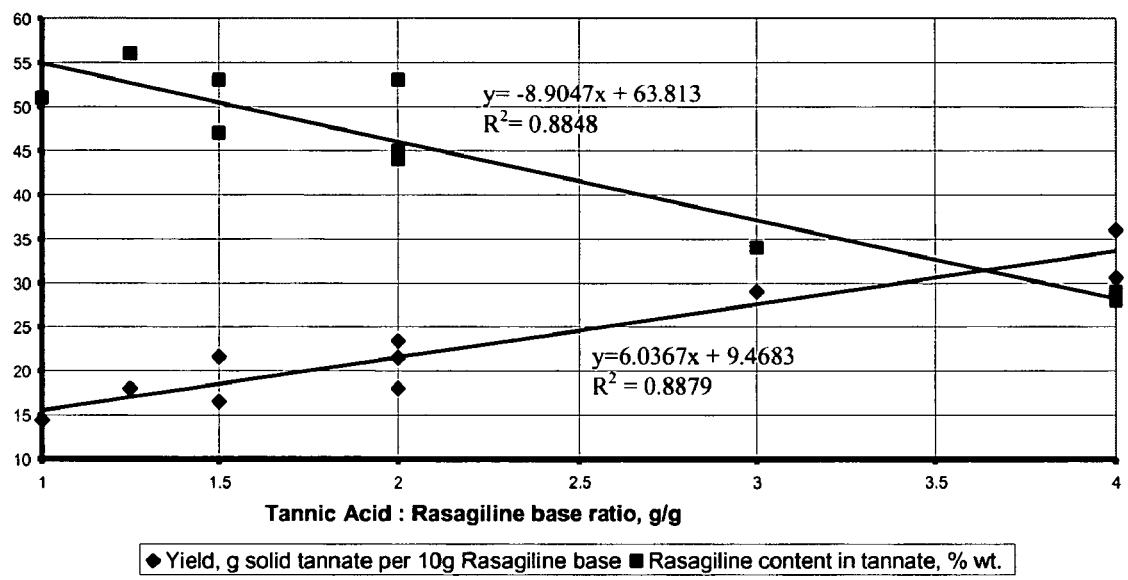
FIG. 1: Effect of tannic acid: rasagiline ratio in aqueous media on rasagiline yield and composition.

The subject invention provides rasagiline tannate.

In an embodiment of the subject invention, the rasagiline tannate content is between 28 and 44% by weight; or between 34 and 44% by weight. By percent by weight, it is meant that all tenth and integer percentages within the range are specifically disclosed as part of the invention. Thus, 28.1, 28.2 . . . 43.8, 43.9; 29, 30 . . . 42, 43 percent of the rasagiline tannate content are included as embodiments of this invention.

The embodiment can further be characterized by an infrared spectrum comprising peaks at the following points: 1498, 1602, 2133, 2852, and 3285 cm$^{-1}$; and the water content of the salt, as determined by Karl Fisher analysis is less than 10% by weight. By percent by weight, it is meant that all tenth and integer percentages within the range are specifically disclosed as part of the invention. Thus, 0.1, 0.2 . . . 9.8, 9.9; 1, 2 . . . 8, 9 percent of water content by weight are included as embodiments of this invention.

The subject invention also provides a composition comprising rasagiline tannate and a carrier.

In an embodiment, the composition is free of rasagiline base that is not ionically bonded to the tannate.

In another embodiment, the composition is free of tannic acid.

In yet another embodiment, the composition is a pharmaceutical composition and the carrier is a pharmaceutically acceptable carrier.

In yet another embodiment, the pharmaceutical composition is in the form of an oral dosage form.

The subject invention also provides a process for the manufacture of rasagiline tannate which comprises: a) combining a solution of tannic acid with rasagiline base to form a first mixture; b) removing at least part of the liquid from the first mixture; c) adding a polar, water soluble solvent to the mixture to form a second mixture; and d) completely removing liquid at ambient temperature from the second mixture.

In an embodiment, the polar, water soluble solvent is ethanol.

In another embodiment, the liquid removing of step b) is performed by decantation.

Rasagiline tannate is a novel salt, which unlike other salts of rasagiline, has low water solubility. This salt may be used for various types of pharmaceutical dosage forms including transdermal and delayed or extended release oral pharmaceutical dosage forms. These types of dosage forms may increase patient compliance.

Tannate salt complexes of active ingredients have been found to have better organoleptic properties such as taste, in comparison to other salts or free base forms. See e.g. U.S. Pat. No. 6,869,618.

EXPERIMENTAL DETAILS

Tannic acid (Tannin) pharmaceutical grade (USP, EP) manufactured by Merck (Merck KGaA, 64271, Darmstadt, Germany) was used in the following examples.

Solid crystalline rasagiline base in the following examples was prepared as follows:

A) Preparation of Rasagiline Base Oil 120 g of rasagiline mesylate (R(+)-N-propargyl-1-aminoindan mesylate) were dissolved in 700 ml of deionized water. 400 ml of toluene were added and the mixture was basified with 25% NaOH solution to a pH of about 14. After stirring, two phases separated. The lower water phase was extracted with 200 ml of toluene. The phases were allowed to separate and the aqueous phase was discarded.

The two toluenic extractions were combined and the solvent was distilled under vacuum. The yield of rasagiline base was 88.5 g of a yellowish oil with a melting point of below 20° C.

B) Crystallization of Rasagiline Base 148 g of rasagiline base oil prepared as described above were dissolved in 180 ml of isopropanol. The solution was cooled to 17° C. and 252 ml of deionized water were added at this temperature. The solution was cooled to 10° C. and seeded with solid rasagiline base. Immediate crystallization was observed. 100 ml of water were then added to the mixture. The mixture was cooled to 1° C., stirred at this temperature for 30 min and filtered. The solid was washed on the filter with 200 ml of water and dried under vacuum.

In the following examples, rasagiline base, mesylate and tartrate were reacted with tannic acid in aqueous media and in polar and non-polar organic solvents. The resulting solid rasagiline tannates were isolated from the reaction mixture by filtration or by settling followed by decantation of liquid layers.

The tannic acid to rasagiline ratio in the examples was between 1 and 4 g/g, and the reaction temperature was between 0° and 45° C.

Parameters and results of the experiments are summarized in Table 1.

Samples of rasagiline tannate prepared in these experiments were subjected to analysis. In each experimental batch the solid product was ground in a mortar and the resulting powder was analyzed by HPLC for rasagiline base content. The products of example 1 and 3-8 were analyzed by physical methods for the solid characterization to determine presence of rasagiline free base and tannic acid.

Particle morphology was studied by microscopic observation of the powders and crystallinity was tested using powder X-ray diffraction (XRD) and Differential Scanning Calorimetry (DSC) methods.

Thermal gravimetric analysis (TGA) was applied for measuring amounts of volatiles (residual solvents and water) in the solid. Water content was measured by Karl Fischer method (KF).

The products of all of the examples below appeared as brown, flowable powder unless otherwise indicated.

EXAMPLE 1

Rasagiline Base (Solid) and Tannic Acid Solution

Solution of 0.5 g Tannic acid in 20 ml water was prepared, 0.5 g of solid crystalline rasagiline base was added slowly to the solution at while stirring, and the color and viscosity change was observed. The resulting suspension was stirred for 1 hr and filtered, the solid washed with water. The solid product was dried under vacuum to a constant weight.

Yield: 0.72 g

A mixture of amorphous rasagiline tannate, tannic acid, and crystalline rasagiline base was formed. The rasagiline content was 51% by weight.

EXAMPLE 2

Rasagiline Base Solution and Tannic Acid Solution

Solutions of 0.5 g solid crystalline rasagiline base in 5 ml ethanol and 0.5 g Tannic acid in 20 ml water were prepared. The ethanolic solution was added slowly to the aqueous solution while stirring and sticky semi-solid material precipitated. Most of the product adhered to the flask and stirrer, the experiment products were discarded.

EXAMPLE 3

Decantation, Ethanol Evaporation

A solution of 1.0 g tannic acid in 20 ml water was prepared and 0.5 g of crystalline rasagiline base was added slowly to the solution while stirring. The mixture was heated to 36° C. Sticky semi-solid material precipitated, and the stirrer was stopped and the precipitate was allowed to settle. The liquor above the sediment was decanted and 20 ml ethanol were added to the sediment and the mixture was stirred. The resulting mixture was transferred to an evaporation flask and evaporated to dryness under vacuum. The residual solid was ground and dried under vacuum to a constant weight.

Yield: 1.17 g

Pure amorphous rasagiline tannate was formed. The rasagiline content was 44% by weight.

EXAMPLE 4

Decantation, Ethanol-Water Evaporation

A solution of 1.5 g tannic acid in 20 ml water was prepared and 0.5 g of solid crystalline rasagiline base was added slowly to the solution while stirring. A sticky semi-solid material precipitated. The stirrer was stopped and the precipitate was allowed to settle. The liquor above the sediment was decanted and 10 ml of ethanol were added to the sediment. The mixture was heated to 38° C. and stirred until dissolution. Water was added dropwise to the mixture and precipitation was observed. The resulting suspension was transferred to the evaporation flask and evaporated to dryness under vacuum. The residual solid was ground and dried under vacuum to a constant weight.

Yield: 1.45 g

Pure amorphous rasagiline tannate was formed. The rasagiline content was 34% by weight.

EXAMPLE 5

Decantation, Ethanol Evaporation

Solutions of 0.5 g solid crystalline rasagiline base in 5 ml ethanol and 2.0 g tannic acid in 20 ml water were prepared. The ethanolic solution was added slowly to the aqueous solution while stirring, and sticky semi-solid material precipitated. The stirrer was stopped and the precipitate was allowed to settle. The liquor above the sediment was decanted and 10 ml ethanol were added to the sediment. The mixture was heated to 40° C. and stirred until dissolution, transferred to an evaporation flask and evaporated to dryness under vacuum. The residual solid was ground and dried under vacuum to a constant weight.

Yield: 1.8 g

A mixture of amorphous rasagiline tannate and tannic acid was formed. The rasagiline content was 28% by weight.

EXAMPLE 6

Decantation, Ethanol Evaporation

Solutions of 1.0 g crystalline rasagiline base in 10 ml isopropanol and 4.0 g tannic acid in 40 ml water were prepared. The isopropanolic solution was added slowly to the aqueous solution while stirring, and a sticky semi-solid material precipitated. The stirrer was stopped and the precipitate was settled. The liquor above the sediment was decanted and 20 ml ethanol was added to the sediment. The mixture was heated to 40° C. and stirred until dissolution, transferred to an evaporation flask and evaporated to dryness under vacuum. The residual solid was ground and dried under vacuum to a constant weight.

Yield: 3.06 g

A mixture of amorphous rasagiline tannate and tannic acid was formed. The rasagiline content was 29% by weight.

EXAMPLE 7

Rasagiline Base and Tannic Acid Solution Cooling

A solution of 2.0 g tannic acid in 30 ml water was prepared and cooled to 0-5° C., then 1.0 g of solid crystalline rasagiline base was added slowly to the solution while stirring. The color and the viscosity of the mixture changed. The resulting suspension was stirred for 30 minutes while cooling and was filtered. The solid was washed with water. During the washing, the solid became sticky and the filtration rate dropped. The solid product was dried under vacuum to constant weight.

Yield: 2.15 g

A mixture of amorphous rasagiline tannate, tannic acid, and crystalline rasagiline base was formed. The rasagiline content was 45% by weight.

EXAMPLE 8

Rasagiline Base and Tannic Acid Solution Cooling

A solution of 1.5 g tannic acid in 30 ml of water was prepared and cooled to 0-5° C., then 1.0 g of crystalline rasagiline base was added slowly to the solution while stirring. The color and the viscosity of the mixture changed. The resulting suspension was stirred for 30 minutes while cooling and was filtered. The resulting solid was washed with water. The solid product was dried under vacuum to a constant weight.

Yield: 1.65 g

A mixture of amorphous rasagiline tannate, tannic acid, and crystalline rasagiline base was formed. The rasagiline content was 53% by weight.

EXAMPLE 9

Solid Rasagiline Base and Tannic Acid Solution

A solution of 0.75 g tannic acid in 30 ml of water was prepared. 0.5 g of solid crystalline rasagiline base was added slowly to the solution while stirring. The resulting mixture was stirred for 2 hours and filtered. The solid was washed with water. The solid product was dried under vacuum to a constant weight. This dried product was designated Sample 1.

The filtrate and wash were combined and evaporated to dryness under vacuum. The residue after evaporation was dried under vacuum to a constant weight. The dried product was designated Sample 2.

Sample 1—Yield—1.08 g, Rasagiline base content 47% by weight.

Sample 2—Yield—0.2 g, Rasagiline base content 24% by weight.

EXAMPLE 10

Solid Rasagiline Base and Tannic Acid Solution

A solution of 1.0 g tannic acid in 30 ml water was prepared and 0.5 g of solid crystalline rasagiline base was added slowly to the solution while stirring. The resulting mixture was stirred for 2 hours and filtered, and a semi-solid fraction resulted. The product was washed with water and dried under vacuum to a constant weight. The dried product was designated Sample 1.

The filtrate and wash were combined and evaporated to dryness under vacuum. The residue after evaporation was dried under vacuum to a constant weight and was designated Sample 2.

Sample 1—Yield—0.9 g, Rasagiline base content 53% by weight.

Sample 2—Yield—0.5 g Rasagiline base content 12% by weight.

EXAMPLE 11

Solid Rasagiline Base and Tannic Acid Solution

A solution of 1.0 g tannic acid in 60 ml water was prepared. 1.0 g of solid crystalline rasagiline base was added slowly to the solution while stirring. The resulting mixture was stirred for 2 hours and was filtered, and a semi-solid fraction resulted. The product was washed with water and dried under vacuum to constant weight. The dried product was designated Sample 1.

The filtrate and wash were combined and evaporated to dryness under vacuum. The residue after evaporation was dried under vacuum to constant weight and was designated Sample 2.

Sample 1—Yield—1.66 g, Rasagiline base content 64% by weight.

Sample 2—Yield—0.24 g, Rasagiline base content 19% by weight.

EXAMPLE 12

Solid Rasagiline Base and Tannic Acid Solution

A solution of 1.25 g tannic acid in 50 ml water was prepared and 1.0 g of solid crystalline rasagiline base was added slowly to the solution while stirring. The resulting mixture was stirred for 2 hours and was filtered. A semi-solid fraction resulted. The product was washed with water and was dried under vacuum to constant weight. The dried product was designated Sample 1.

The filtrate and wash were combined and evaporated to dryness under vacuum. The residue after evaporation was dried under vacuum to a constant weight and was designated Sample 2.

Sample 1—Yield—1.8 g, Rasagiline base content 56% by weight.

Sample 2—Yield—0.3 g, Rasagiline base content 20% by weight.

EXAMPLE 13

Reaction between Rasagiline Mesylate and Tannic Acid

A solution of 3.0 g tannic acid in 30 ml water was prepared and then 1.5 g of rasagiline mesylate was added slowly to the solution while stirring. Complete dissolution of the solid was observed at ambient temperature.

A drop of 25% NaOH solution was added to the mixture. Immediate precipitation took place. The batch was discarded.

EXAMPLE 14

Reaction Between Rasagiline Tartrate and Tannic Acid

Solution of 2.8 g tannic acid in 30 ml water was prepared and then 1.44 g of rasagiline tartrate was added slowly to the solution at stirring. Precipitation of an oily, sticky product was observed. The batch was discarded.

EXAMPLE 15

Reaction in Ethyl Acetate

A mixture of 0.5 g solid rasagiline base, 2.0 g of tannic acid and 30 ml ethyl acetate was stirred for 2 hours. The resulting suspension was filtered and the solid was washed on the filter with ethyl acetate and was dried under vacuum.

Yield—1.7 g

EXAMPLE 16

Reaction in Ethyl Acetate

A mixture of 0.5 g solid rasagiline base, 2.0 g of tannic acid and 30 ml ethyl acetate was stirred for 2 hours. The resulting suspension was filtered and the solid was dried under vacuum.

Yield—1.7 g

EXAMPLE 17

Reaction in Ethyl Acetate

A solution of 0.5 g solid rasagiline base in 10 ml ethyl acetate was introduced into a suspension of 2.0 g of tannic acid in 30 ml of ethyl acetate at 45° C. The mixture was stirred for 2 hours at 45° C. and the resulting suspension cooled to 0-5° C. and filtered. The solid product was dried under vacuum and was designated Sample 1.

The filtrate and wash were combined and evaporated to dryness under vacuum. The residue after evaporation was dried under vacuum to constant weight and was designated Sample 2.

Sample 1—Yield—0.28 g, Rasagiline base content 19% by weight.

Sample 2—Yield—2.33 g, Rasagiline base content 26% by weight.

EXAMPLE 18

Reaction in Ethyl Acetate

A mixture of 0.5 g solid rasagiline base, 2.0 g of tannic acid, and 30 ml ethyl acetate was stirred for 6 hours. The resulting suspension was filtered and the solid was washed on the filter with ethyl acetate and dried under vacuum. The dried solid was designated Sample 1.

The filtrate and wash were combined and evaporated to dryness under vacuum. The residue after evaporation was dried under vacuum to a constant weight and was designated Sample 2.

Sample 1—Yield—1.7 g, Rasagiline base content 3% by weight.

Sample 2—Yield—0.83 g, Rasagiline base content 63% by weight.

EXAMPLE 19

Reaction in Ethyl Acetate 0.5 g solid rasagiline base and 2.0 g of tannic acid were mixed with 30 ml ethyl acetate and heated to 45° C. The mixture was stirred for 1.25 hrs at 45° C. and the resulting suspension cooled to 0-5° C. and filtered. The solid product was washed with ethyl acetate and dried under vacuum and was designated Sample 1.

The filtrate and wash were combined and evaporated to dryness under vacuum. The residue after evaporation was dried under vacuum to a constant weight and was designated Sample 2.

Sample 1—Yield—0.8 g, Rasagiline base content 9% by weight.

Sample 2—Yield—1.9 g, Rasagiline base content 33% by weight.

EXAMPLE 20

Reaction in Hexane 0.5 g solid rasagiline base was dissolved in 50 ml hexane. 1.5 g of tannic acid was added to the solution. The mixture was stirred for 2 hours and filtered. The solid product was washed with hexane and dried under vacuum and designated Sample 1.

The filtrate and wash were combined and evaporated under vacuum to dryness. The solid residue was a colorless crystalline material, designated Sample 2.

Sample 1—Yield—1.46 g, Rasagiline base content 3% by weight.

Sample 2—Yield—0.52 g, pure crystalline Rasagiline base (m.p. 39.0-39.3° C.)

The results of the example 20 show that in non-polar solvent (hexane) rasagiline base does not substantially react with Tannic acid. Unreacted pure Rasagiline base crystallizes from the filtrate during evaporation.

SUMMARY OF RESULTS

The rasagiline base content, composition, hygroscopicity and water content of the products of the examples are listed in the table below.

TABLE 1

| | Physical properties and composition of rasagiline tannate | | | | |
|---|---|---|---|---|---|
| | | | | Water content, % | |
| Example | Rasagiline base content % | Crystallinity, composition by XRD and DSC | Hygroscopicity | By TGA | By KF |
| Rasagiline base | 100 | Crystalline rasagiline base | 1 | L.T. 0.1 | 0.1 |

TABLE 1-continued

Physical properties and composition of rasagiline tannate

| Example | | Rasagiline base content % | Crystallinity, composition by XRD and DSC | Hygroscopicity | Water content, % By TGA | By KF |
|---|---|---|---|---|---|---|
| Tannic acid | | 0 | Amorphous TA | 1 | 7.1 | 10.0 |
| 1 | | 51 | Mixture of amorphous RT, TA and crystalline rasagiline base | 3 | 3.5 | 3.8 |
| 3 | | 44 | Amorphous RT | 1 | 3.4 | 3.4 |
| 4 | | 34 | Amorphous RT | 1 | 5.2 | 4.5 |
| 5 | | 28 | Amorphous RT and TA | 1 | 4.5 | 6.3 |
| 6 | | 29 | Amorphous RT and TA | 1 | 3.8 | 5.4 |
| 7 | | 45 | Mixture of amorphous RT, TA and crystalline rasagiline base | 2 | 4.8 | 6.3 |
| 8 | | 53 | Mixture of amorphous RT, TA and crystalline rasagiline base | 3 | 2.1 | 4.8 |
| 9 | Sample 1 | 47 | N.A. | 2 | N.A. | N.A. |
|   | Sample 2 | 24 | N.A. | 1 | N.A. | N.A. |
| 10 | Sample 1 | 53 | N.A. | 3 | N.A. | N.A. |
|   | Sample 2 | 12 | N.A. | 1 | N.A. | N.A. |
| 11 | Sample 1 | 64 | N.A. | 4 | N.A. | N.A. |
|   | Sample 2 | 19 | N.A. | 1 | N.A. | N.A. |
| 12 | Sample 1 | 56 | N.A. | 2 | N.A. | N.A. |
|   | Sample 2 | 20 | N.A. | 1 | N.A. | N.A. |
| 17 | Sample 1 | 19 | N.A. | 1 | N.A. | N.A. |
|   | Sample 2 | 26 | N.A. | 1 | N.A. | N.A. |
| 18 | Sample 1 | 3 | N.A. | 1 | N.A. | N.A. |
|   | Sample 2 | 63 | N.A. | 4 | N.A. | N.A. |
| 19 | Sample 1 | 9 | N.A. | 1 | N.A. | N.A. |
|   | Sample 2 | 33 | N.A. | 1 | N.A. | N.A. |
| 20 | Sample 1 | 3 | N.A. | 1 | N.A. | N.A. |
|   | Sample 2 | 100 | Crystalline rasagiline base | 1 | N.A. | N.A. |

N.A.—not available
RT—rasagiline tannate
TA—tannic acid
TGA—thermal gravimetric analysis
KF—Karl Fischer analysis The hygroscopicity was determined after one month in closed containers at room temperature in atmospheric air (relative humidity ~50-80%)

The observed samples could be divided into four groups in accordance to their hygroscopic properties:

1=non-hygroscopic, no visible change observed

2=slightly hygroscopic, aggregation and lumping developed, loss of flowability

3=hygroscopic, semi-solid material

4=deliquescent, liquefied syrup-like product

A strong correlation was present between the hygroscopic behavior of the samples and rasagiline content in the tannate salt samples. Samples with rasagiline content of less than 45% do not demonstrate hygroscopic behavior, while samples with more than 45% rasagiline. As the rasagiline content in the sample increases, the hygroscopicity also increases.

DISCUSSION

Preparation of a tannate salt of an active pharmaceutical is not a routine endeavor. Tannate salts are difficult to make and to work with. Even if a tannate salt can be made, each active pharmaceutical presents its own unique problems when being made into a tannate salt, which problems cannot be readily foreseen before attempting to make the tannate salt. Even if a tannate salt can be successfully made, its properties and practicality for pharmaceutical use might be unacceptable. The specific issues of preparing and the properties of rasagiline tannate are discussed below.

Characterization and Yield of Rasagiline Tannate

The data presented demonstrates that a higher ratio of tannic acid to rasagiline provides higher yield of rasagiline tannate. It is also evident that the rasagiline tannate yield is affected by the isolation technique. The batches prepared in aqueous or aqueous/alcohol media by filtration had lower yields compared to the batches prepared by decantation and evaporation. The yield of the filtration batches is within the range of 1.44-2.15 g/g rasagiline, and the decantation batches have the yield of 2.24-3.6 g/g rasagiline. A possible reason for this phenomenon is that following:

When filtration is used to separate the solids from the mother liquor, all the mother liquor is separated from the precipitate. When decantation is used, some of the liquor with the dissolved substance remains with the precipitate. During the evaporation the dissolved material precipitates as solid and increases the yield.

Examples 15-20 show that preparation of rasagiline tannate in non-polar organic solvent is not feasible. Products of reactions performed in ethyl acetate and in hexane have low rasagiline content in the solid product. Experiments 17-20 demonstrate that most of the rasagiline remains in the filtrates. The solid products collected by filtration in these experiments contain only 3-19% rasagiline. Experiments 15, 16 and 18 performed in ethyl acetate at lower temperatures gave higher yield of the solid product, possible as a result of incomplete reaction between rasagiline and tannic acid.

As evident in example 20, the reaction between rasagiline base and tannic acid in hexane does not take place despite the solubility of rasagiline base in hexane. The solid product contains only 3% rasagiline and practically all of the rasagiline base remains in the reaction liquor. At the same time the filtered liquor did not contain any tannic acid.

A similar phenomenon of incomplete reaction was found in the experiments performed in aqueous media. Reactions that were performed at low temperatures (experiments 1, 7 and 8) resulted in a mixture of amorphous rasagiline tannate, tannic acid and unreacted crystalline rasagiline base. Free crystalline rasagiline base was detected in these samples of rasagiline tannate by XRD and FTIR techniques. DSC analysis of these samples also showed a characteristic endothermal peak related to the melting of rasagiline base at 40° C.

Amorphous samples of rasagiline tannate from examples 3-6 do not contain free rasagiline base. Samples from examples 1, 5, 6 and 7 were determined by DSC contain a small peak related to free tannic acid. A sample from example 8 contained only small amounts of free tannic acid. Samples from examples 3 and 4 did not contain a detectable amount of either tannic acid or free rasagiline base. These two samples (Experiments 3 and 4) represent pure rasagiline tannate without inclusions of free acid and free base.

Rasagiline tannate appears under a microscope as irregular solid particles. Since the material is an amorphous solid of variable composition it could be a solid solution, inclusion complex or any other type of physical mixture. Rasagiline tannate was determined by XRD to be an amorphous salt.

FTIR spectra of tannic acid, solid rasagiline base and pure rasagiline tannate from example 3 were compared. The comparison is summarized in Table 2.

TABLE 2

FTIR patterns of rasagiline tannate, tannic acid and rasagiline base.
IR peaks appears in spectra, $cm^{-1}$

| Rasagiline base | Tannic acid; USP, Merck | Rasagiline tannate |
|---|---|---|
| 564; 611; 693; 1963; 1976; 2873; 3381 | No | No |
| No | 1039 | No |
| No | No | 1498; 1602; 2133; 2852; 3285 |

A Perkin Elmer Spectrum One FT-IR Spectrometer S/N 58001 was used. The samples were studied in DRIFT mode. All the spectra were measured in 16 scans. Resolution was 4.0 $cm^{-1}$.

The spectra demonstrate that the sample of rasagiline tannate that does not contain detectable amounts of rasagiline base and tannic acid has significant difference in IR spectra. Peaks at 1498, 1602, 2133, 2852 and 3285 $cm^{-1}$ were found to be characteristic for rasagiline tannate.

FTIR results show that experiments 3 and 4 gave pure Rasagiline tannate since no peaks related to Tannic acid or Rasagiline base are detected in the solids. This finding is in agreement with the XRD and DSC results and it proves unequivocally that these experiments provide pure amorphous tannate salt of rasagiline.

Composition of Rasagiline Tannate

There is no constant stoichiometric ratio between the amine base and tannic acid in rasagiline tannate. In the tannates prepared in aqueous media the content of rasagiline base varied between 28 and 64% by weight. This fact could be explained by the chemical nature of tannic acid: Pharmaceutical grade tannic acid is a complex mixture of tannins containing few (three or more) types of acidic functional groups of phenolic nature. These acidic groups have different pKa value and are able to react with amine bases forming insoluble tannate salts. Reaction of a part of the phenolic groups with amine base at low ratio of base to tannic acid causes precipitation of insoluble tannate. Thus, different acid to base ratios at the precipitation step causes precipitation of tannate salts of different composition.

The tannates with different composition have different hygroscopic properties, as shown above. Complete substitution of the acidic groups in tannic acid with rasagiline base causes formation of a hygroscopic product. The empirical data shown in Table 1 demonstrate that rasagiline tannate having more than 45% by weight of rasagiline base is hygroscopic. Higher content of the base in the salt results in higher hygroscopicity of the solid.

The graph presented in FIG. 1 demonstrates the effect of the ratio between tannic acid and rasagiline base on the yield and composition of rasagiline tannate.

The data shows that higher tannic acid to rasagiline ratio is responsible for a higher amount (mass yield) of rasagiline tannate that is precipitated in aqueous media. At the same time the content of rasagiline base in tannate salt is lower when the salt is formed at higher tannin to base ratio.

The FIG. 1 is based on the results of the experiments 1-12 presented in table 1. In spite of the fact that different methods of rasagiline tannate isolation applied in these experiments, good correlation between tannin to rasagiline ratio and composition and yield of rasagiline tannate was found ($R2>0.88$). This finding provides control of the tannate DS composition by varying of tannin to base ratio at the precipitation step.

CONCLUSIONS

A new salt, rasagiline tannate was prepared, characterized and found practical for pharmaceutical development. It was proven that rasagiline tannate is an amorphous salt of variable composition.

Two methods of rasagiline tannate isolation from the reaction mixture were evaluated. Both methods, decantation and filtration, were found to be feasible. However, the decantation method provided higher yield of rasagiline tannate.

The effect of rasagiline base to tannic acid ratio on rasagiline tannate hygroscopic properties was established. It was found that rasagiline tannate containing more than 45% rasagiline base is hygroscopic and higher content of the base provide higher hygroscopicity of the tannate.

Presence of free rasagiline base and free tannic acid was found and characterized in some samples of rasagiline tannate. In examples 3 and 4, it has been shown that it has been possible to prepare the salt free of solid rasagiline base and tannic acid.

Since the composition of rasagiline tannate is variable and depends on reactant ratio and isolation conditions, optimal rasagiline content in rasagiline tannate was established between 28 and 44%.

What is claimed is:

1. Rasagiline tannate.

2. The rasagiline tannate of claim 1 wherein the rasagiline content is between 28 and 44% by weight.

3. The rasagiline tannate of claim 1 wherein the rasagiline content is between 34 and 44% by weight.

4. The rasagiline tannate of claim 1 characterized by an infra-red spectrum comprising peaks at the following points: 1498, 1602, 2133, 2852 and 3285 cm$^{-1}$.

5. The rasagiline tannate of claim 1 wherein the water content of the salt, as determined by Karl Fischer analysis is less than 10%.

6. A composition comprising the rasagiline tannate of claim 1 and a carrier.

7. The composition of claim 6, wherein the composition is free of rasagiline base that is not ionically bonded to the tannate.

8. The composition of claim 6, wherein the composition is free of tannic acid.

9. The composition of claim 6, wherein the composition is a pharmaceutical composition and the carrier is a pharmaceutically acceptable carrier.

10. The pharmaceutical composition of claim 9 in the form of an oral dosage form.

11. A process for manufacture of rasagiline tannate comprising:
   a. combining a solution of tannic acid with rasagiline base to form a first mixture;
   b. removing at least part of the liquid from the first mixture;
   c. adding a polar, water soluble solvent to the mixture to form a second mixture; and
   d. completely removing liquid at ambient temperature from the second mixture.

12. The method of claim 11, wherein the polar, water soluble solvent is ethanol.

13. The method of claim 11 wherein the liquid removing of step b) is performed via decantation.

* * * * *